United States Patent [19]
Lenker et al.

[11] Patent Number: 5,749,921
[45] Date of Patent: May 12, 1998

[54] APPARATUS AND METHODS FOR COMPRESSION OF ENDOLUMINAL PROSTHESES

[75] Inventors: Jay A. Lenker, Los Altos Hills; Michael A. Evans, Palo Alto; Steven W. Kim, Sunnyvale, all of Calif.; Edward V. Kinney, Louisville, Ky.

[73] Assignee: Medtronic, Inc., Minneapolis, Minn.

[21] Appl. No.: 603,755

[22] Filed: Feb. 20, 1996

[51] Int. Cl.$^6$ ..................................................... A61F 2/06
[52] U.S. Cl. ......................... 623/1; 606/194; 606/195
[58] Field of Search .................... 623/1, 12; 606/194, 606/195

[56] References Cited

U.S. PATENT DOCUMENTS

| | | | |
|---|---|---|---|
| 4,512,338 | 4/1985 | Balko et al. | 128/1 R |
| 4,990,151 | 2/1991 | Wallstén | 606/108 |
| 4,998,539 | 3/1991 | Delsanti | 606/194 |
| 5,035,706 | 7/1991 | Giantureo et al. | 623/1 |
| 5,123,917 | 6/1992 | Lee | 623/1 |
| 5,221,261 | 6/1993 | Termin et al. | 606/194 |
| 5,360,443 | 11/1994 | Barone et al. | 623/1 |
| 5,366,504 | 11/1994 | Andersen et al. | 623/1 |
| 5,375,612 | 12/1994 | Cottenceau et al. | 606/194 |
| 5,378,239 | 1/1995 | Termin et al. | 606/194 |
| 5,387,235 | 2/1995 | Chuter | 623/1 |
| 5,433,723 | 7/1995 | Lindenberg et al. | 606/198 |
| 5,480,423 | 1/1996 | Ravenscroft et al. | 606/194 |
| 5,496,277 | 3/1996 | Termin et al. | 606/194 |
| 5,499,995 | 3/1996 | Teirstein | 606/192 |
| 5,507,767 | 4/1996 | Maeda et al. | 606/198 |
| 5,562,726 | 10/1996 | Chuter | 623/1 |
| 5,591,195 | 1/1997 | Taheri et al. | 623/1 |

FOREIGN PATENT DOCUMENTS

| | | | |
|---|---|---|---|
| 539237 | 4/1993 | European Pat. Off. | 623/1 |
| 9317636 | 9/1993 | WIPO | 623/1 |
| WO 96/23455 | 8/1996 | WIPO | A61F 2/06 |

OTHER PUBLICATIONS

Brochure from World Medical Manufacturing Corporation. "Graft Removal System." *Talent*, Sunrise, Florida, *Publication Date Unknown*.

World Medical Manufacturing Corporation Internet WEB Page Information, downloaded Aug. 4, 1997.

*Primary Examiner*—Debra S. Brittingham
*Assistant Examiner*—Tram Anh T. Nguyen
*Attorney, Agent, or Firm*—Townsend and Townsend and Crew LLP

[57] ABSTRACT

The present invention provides devices and methods to promote the compression and/or recapture of endoluminal prostheses. An endoluminal prosthesis system generally comprises a tubular body and a radially compressible endoluminal prosthesis. The tubular body includes a lumen, while the prosthesis has a proximal end with a plurality of engageable structures radially disbursed thereabout. Each of a plurality of filaments extends distally from the lumen of the tubular body to an engageable structure so that tensioning of the filaments radially compresses the proximal end of the prosthesis. Preferably, a sheath then slides over the prosthesis, the sheath ideally having a plurality of axially oriented runners which form a radially flared structure to smoothly compress the prosthesis therebetween.

13 Claims, 5 Drawing Sheets

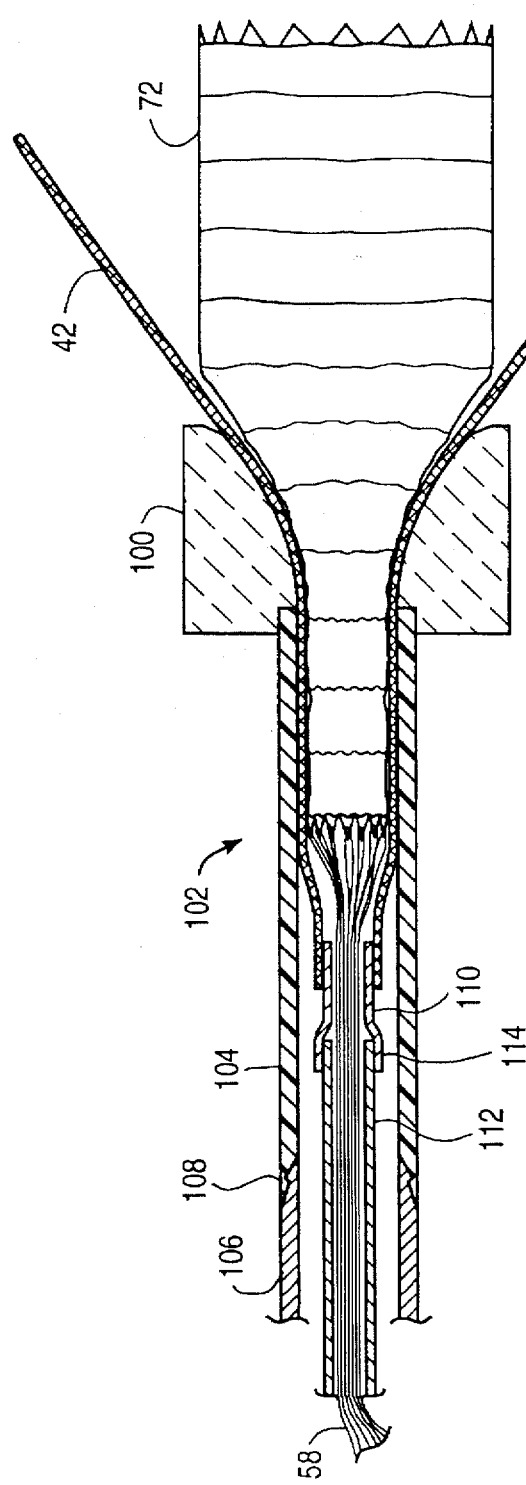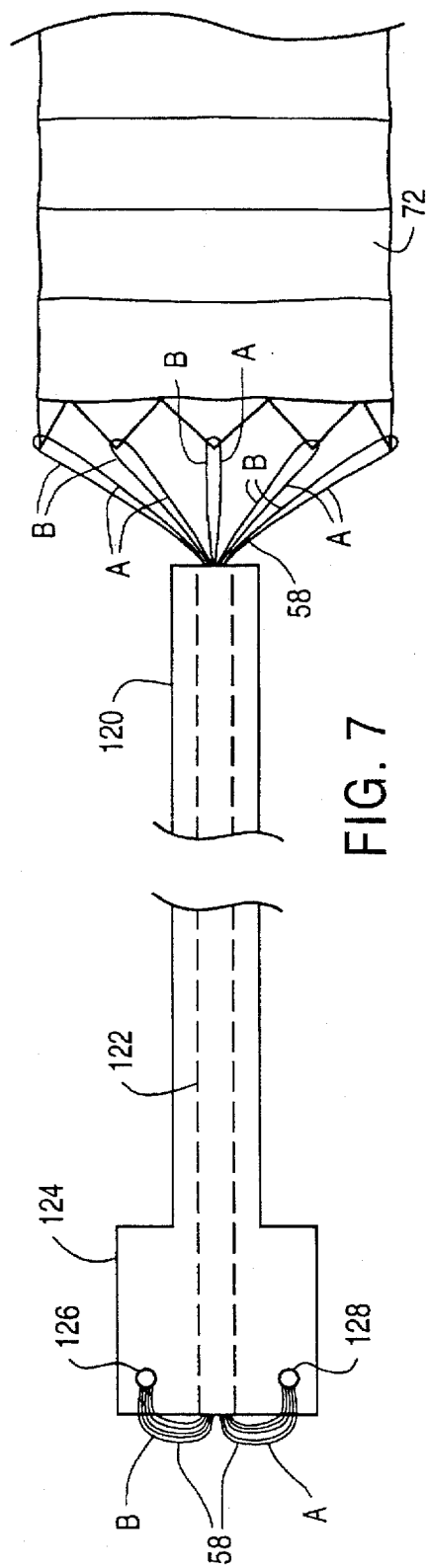

APPARATUS AND METHODS FOR COMPRESSION OF ENDOLUMINAL PROSTHESES

BACKGROUND OF THE INVENTION

1. Field of Invention

The present invention relates generally to endoluminal prostheses, such as stents, stent-grafts, and other structures. More particularly, the present invention provides a prosthesis compression system having a plurality of filaments which pull a radially compressible prostheses inward to facilitate loading the prosthesis into a delivery catheter, or to allow recapture of a prosthesis which has been expanded within a body lumen.

Vascular aneurysms are the result of abnormal dilation of a blood vessel, usually resulting from disease and/or genetic predisposition, which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is bypassed and repaired with an artificial vascular graft. While considered to be an effective surgical technique, particularly considering the alternative of a usually fatal ruptured abdominal aortic aneurysm, conventional vascular graft surgery suffers from a number of disadvantages. The surgical procedure is complex and requires experienced surgeons and well equipped surgical facilities. Even with the best surgeons and equipment, however, patients being treated frequently are elderly and weakened from cardiovascular and other diseases, reducing the number of eligible patients. Even for eligible patients prior to rupture, conventional aneurysm repair has a relatively high mortality rate, usually from 3% to 10%. Morbidity related to the conventional surgery includes myocardial infarction, renal failure, impotence, paralysis, and other conditions. Additionally, even with successful surgery, recovery takes several weeks, and often requires a lengthy hospital stay.

In order to overcome some or all of these drawbacks, endovascular prosthesis placement for the treatment of aneurysms has been proposed. Although very promising, many of the proposed methods and apparatus suffer from other problems. In particular, delivery and placement of the endovascular prosthesis within the vasculature can be problematic. Proper positioning and sizing of the endovascular prosthesis is critical to the successful treatment of an aneurysm. Unfortunately, proper prosthesis sizing and location are difficult to confirm prior to partial or full expansion of the prosthesis within the body lumen. With many endovascular prosthetic structures and their associated delivery catheters, however, it is difficult or impossible to retract an even partially released endoluminal prosthesis. Thus, improper initial placement of a prosthesis can sometimes require open surgical procedures for correction.

Furthermore, endoluminal prostheses are often resilient, biased to expand and anchor the prosthesis within the body lumen. These resiliently expanding structures are tightly compressed within the catheter, imposing significant loading forces on the prosthesis and the surrounding catheter bodies, and often leading to substantial friction between the prosthesis and the catheter wall. These forces complicate the initial loading of the prosthesis into the catheter, and make recapture or repositioning of an improperly deployed prosthesis problematic.

For these reasons, it would be desirable to provide improved systems and methods for compressing intraluminal protheses, including stents and stent-grafts. It would be particularly desirable to provide endoluminal prosthesis systems and methods which permit the retrieval of partially or fully expanded prostheses. It would be further desirable if such systems were able to minimize the substantial frictional forces between the prosthesis and the surrounding catheter structure during compression of the prosthesis, so as to avoid damaging the prosthesis, and to reduce the risk of injury to surrounding tissues.

2. Description of the Background Art

U.S. Pat. No. 5,035,706 describes a percutaneous stent and method for its retrieval. The described stent is formed as a "zig-zag" with eyes formed at the bends at one end. A single thread passes successively through each eye to form at least a 360° loop around the circumference of the stent, preferably forming a loop of 540° around the circumference of the stent. U.S. Pat. No. 5,433,723 describes an endoprosthesis and an associated endoprosthesis applicator for widening a stenosis. The applicator includes an outer sleeve which radially restrains the prosthesis, within which axially separated tongues are optionally disposed over one end of the prosthesis. U.S. Pat. No. 5,387,235 describes an expandable transluminal graft prosthesis and delivery catheter. In some embodiments, mooring loops prevent expansion of the prosthesis prior to actuation of a control means.

SUMMARY OF THE INVENTION

In a first aspect, the present invention provides an endoluminal prosthesis system comprising a tubular body and a radially compressible endoluminal prosthesis. The tubular body includes a lumen, while the prosthesis has an end with a plurality of engageable structures radially disbursed thereabout. Each of a plurality of filament loops extends distally from the lumen of the tubular body to engage an engageable structure, and returns back toward the tubular body. The filaments are capable of drawing the proximal end of the prosthesis radially inward to effect radial compression of the end of the prosthesis when the filaments are tensioned.

Typically, each loop engages the prosthesis at a single location. The engageable structures will generally be defined by a frame of the prosthesis, typically comprising openings adjacent to these proximally oriented apices of the frame. The filaments will generally comprise a polyester yarn, a monofilament, a wire, or the like.

A sheath will often slide distally over the prosthesis when the filaments are tensioned. Preferably, the sheath includes a radially flareable structure at its distal end. In a particularly advantageous embodiment, the flareable structure comprises a plurality of elongate runners which slide into the sheath around the prosthesis, thereby reducing friction between the prosthesis and sheath. Alternatively, fixed flared structures may be used alone or in combination with runners.

In another aspect, the present invention provides a method for radially compressing an endoluminal prosthesis, the method comprising tensioning a plurality of filaments so that each filament draws a portion of an end of an endoluminal prosthesis radially inward toward a lumen of a tubular body. Either the prosthesis or a sheath slides relative to the other so that the sheath passes over the inward drawn end of the prosthesis. Advantageously, such a method may also be performed in situ to recapture an expanded prosthesis. Recapture is facilitated by drawing axial runners into the sheath around the captured prosthesis. Alternatively, the present method may be used to load the prosthesis into a delivery catheter prior to use, optionally (but not necessarily) while maintaining the prosthesis at a reduced temperature to facilitate compression of a shape memory alloy frame. Conveniently, the methods of the present invention allow the prosthesis to be released by cutting the filaments from proximally of the tubular body and withdrawing the free ends proximally.

BRIEF DESCRIPTION OF THE DRAWINGS

FIG. 6 is a cutaway view of a prosthesis being loaded into a prosthetic cartridge having axial runners using a fixed flared structure, according to the principles of the present invention.

FIG. 7 is a schematic illustration of a proximal loop system which facilitates disengaging the prosthesis.

DESCRIPTION OF THE SPECIFIC EMBODIMENT

The present invention provides devices, systems, and methods for the compression of endoluminal tubular prostheses, particularly stents and stent-grafts. The present invention will compress the prostheses to a narrow-diameter configuration, and may be used to load the prosthesis into a catheter prior to introduction into a body lumen. The invention will find further use in recapturing a prosthesis which has been partially or fully expanded within the body lumen.

The systems and methods of the present invention will have applications over a wide variety of therapeutic uses, including stenting of the ureter, urethra, biliary tract, and the like. The invention will also promote the use of endoluminal prostheses for the creation of temporary or long term lumens, such as the formation of fistulas. The present invention will find its most immediate use, however, in facilitating the loading and recapture of endovascular stent-grafts within delivery catheters, thereby improving the safety of endovascular therapies of blood vessels for the treatment of abdominal and other aneurysms, vascular stenoses, and the like.

Although the methods and devices of the present invention are generally described with reference to simple cylindrical prostheses, they will find additional applications to more complex bifurcated and modular prosthetic structures. Exemplary modular and bifurcated prosthesis structures are described in co-pending patent application Ser. Nos. 08/538, 706 and 60/008,254 (Attorney Docket Nos. 16380-003800 and 16380-003400, respectively), the full disclosures of which are incorporated herein by reference. Additionally, while the endoluminal compression devices and methods of the present invention may be used with resilient prosthetic structures, plastically deformable prosthetic structures, or combinations thereof, they will be particularly advantageous when used to compress and/or recapture prosthetic structures which expand resiliently when released within a body lumen.

Figure 1:
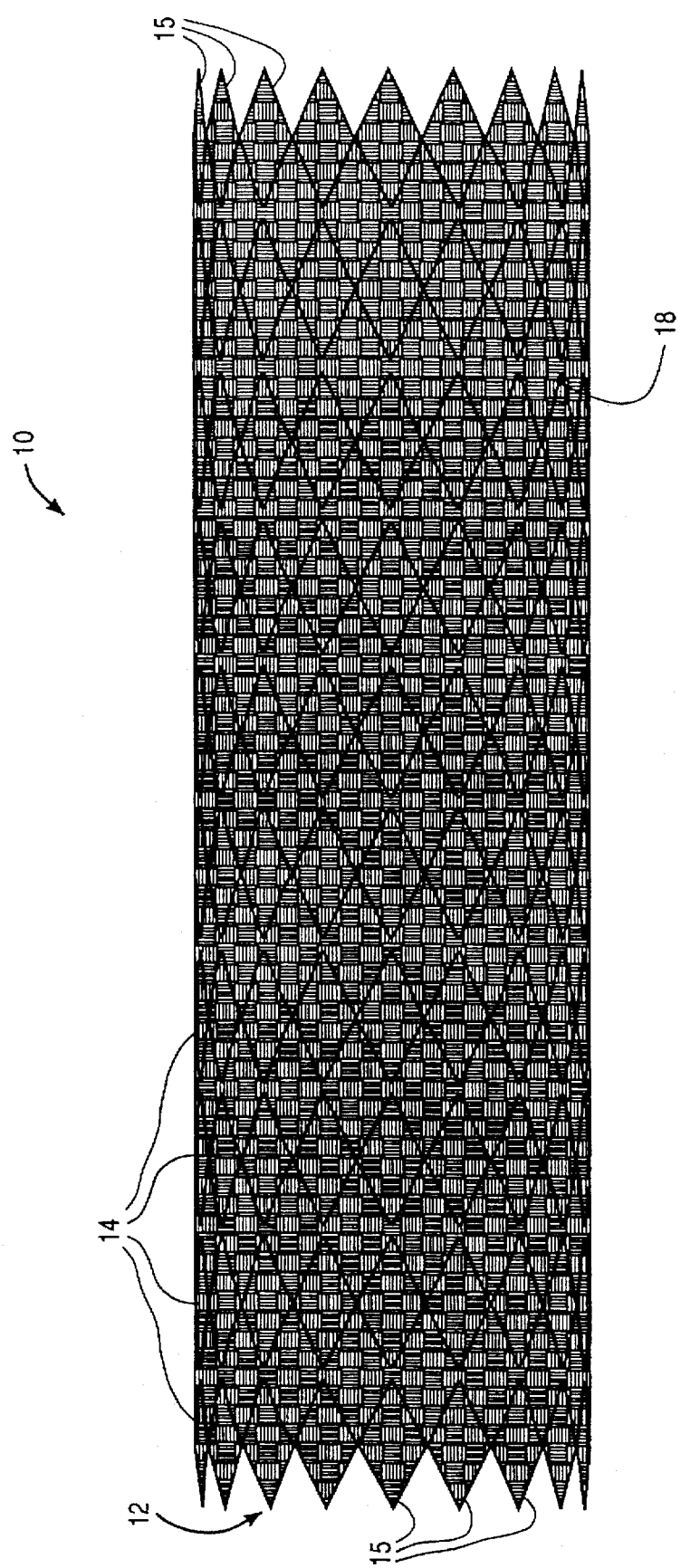
FIG. 1 is a side view of a vascular graft which is exemplary of the type of radially compressible tubular prosthesis which may compressed and/or recaptured using the systems and methods of the present invention.

An exemplary cylindrical graft structure 10 is illustrated in FIG. 1. Prosthesis 10 comprises a perforate tubular frame 12 which includes a plurality of independent (non-connected) ring frames 14. Frame 12 typically comprises a resilient, high strength, biocompatible alloy, preferably a superelastic shape memory alloy such as Nitinol™. The expanded perforate ring frame structures define a number of axially oriented apices 15 at each end. The tubular frame 12 supports an inner liner 18. Optionally, an outer liner is disposed over the ring frames, either instead of inner liner 18, or in combination therewith.

To secure ring frames 14 in place, and to secure the liner to the perforate tubular frame 12, the liner is typically sutured to the frame. A wide variety of alternative liner/frame attachment mechanisms are available, including adhesive bonding, heat welding, ultrasonic welding, and the like. Where inner and outer liners are used, the ring frames may be sandwiched between the liners and held in place by attaching the liners to each other. The liner will generally comprise a continuously woven polyester such as Dacron™, ideally in the form of a plastically expansible yarn, as more fully explained in co-pending U.S. patent application Ser. No. 08/595,944, the full disclosure of which is incorporated herein by reference.

The prosthesis 10 will typically have a length in the range from about 20 mm to 500 mm, preferably from 50 mm to 200 mm, with a relaxed diameter in the range from about 4 mm to 45 mm, preferably being in the range from 5 mm to 38 mm.

Figure 2:
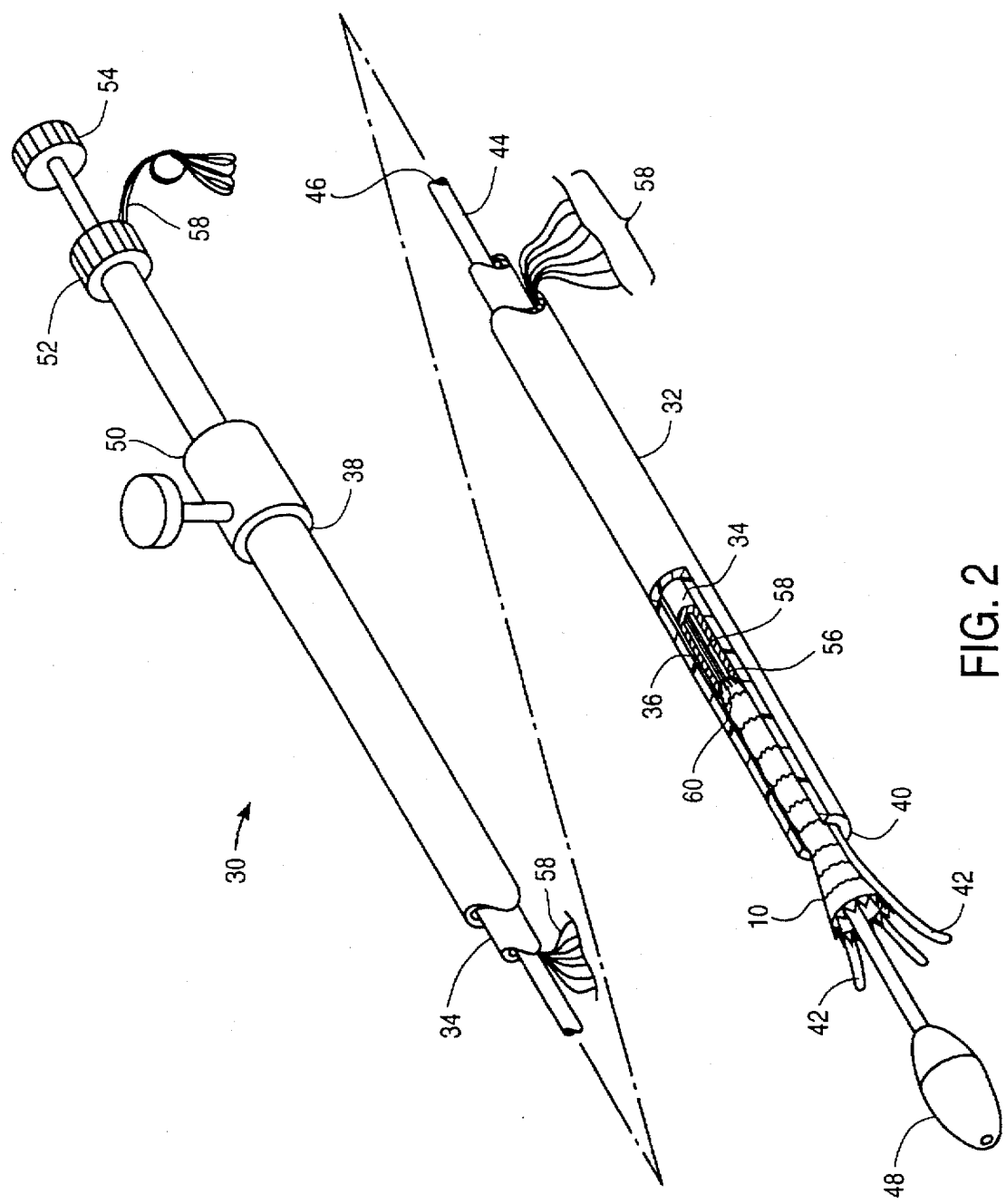
FIG. 2 is a perspective view of a delivery catheter of the present invention, in which a portion of the catheter has been cutaway to illustrate a prothesis therein.

Referring now to FIG. 2, a delivery catheter 30 according to the present invention comprises a tubular sheath 32 and a shaft 34. Sheath 32 has a central lumen 36 extending from a proximal end 38 to a distal end 40. Shaft 34 is slidably received within central lumen 36 and extends proximally of sheath 32.

A plurality of runners 42 can be extended distally from shaft 34. Runners 42 line a portion of the inner surface of lumen 36, and slide within the lumen with the shaft. Shaft 34 also has a lumen 56, in which a core shaft 44 is slidably disposed. Core shaft 44 has a guide wire lumen 46. Nosecone 48 is fixed to the distal end of core shaft 44, and can therefore be manipulated independently of runners 42. Alternatively, the core shaft may be affixed to and manipulated with shaft 36.

Prosthesis 10 is radially compressed and restrained within the plurality of runners 42. In turn, sheath 32 prevents runners 42 from expanding outward. Runners 42 are formed from a thin, relatively hard material, typically comprising a high strength biocompatible alloy such as a shape memory alloy, stainless steel, or a stainless steel alloy, and distribute the expansion load of prosthesis 10 over the inner surface of central lumen 36. The deploying force is applied proximally against a slider 50 attached to distal end 38 of sheath 30, while holding a luer fitting 52 at the distal end of shaft 34, thereby withdrawing the sheath proximally from over the prosthesis. An additional luer adaptor 54 at the distal end of core shaft 44 allows the core shaft to be manipulated independently, and to be releasably secured to the shaft 34.

The attachment, structure, and use of the runners for the deployment of endoluminal prostheses are more fully explained in co-pending U.S. patent application Ser. No. 08/475,200 (Attorney Docket No. 16380-001130), the full disclosure of which is incorporated herein by reference.

A plurality of filament loops 58 are disposed within lumen 56 of shaft 34. Each of the loops extends radially outward from the lumen of the shaft adjacent a proximal end 60 of prosthesis 10, where the loops pass through a frame of the prosthesis and then return proximally through lumen 56. The loops generally extend proximally beyond the shaft, and may conveniently be attached together, or may be affixed to a proximal handle or actuator to facilitate application of a uniform tension to compress the prosthesis after it is released.

Figure 3A:
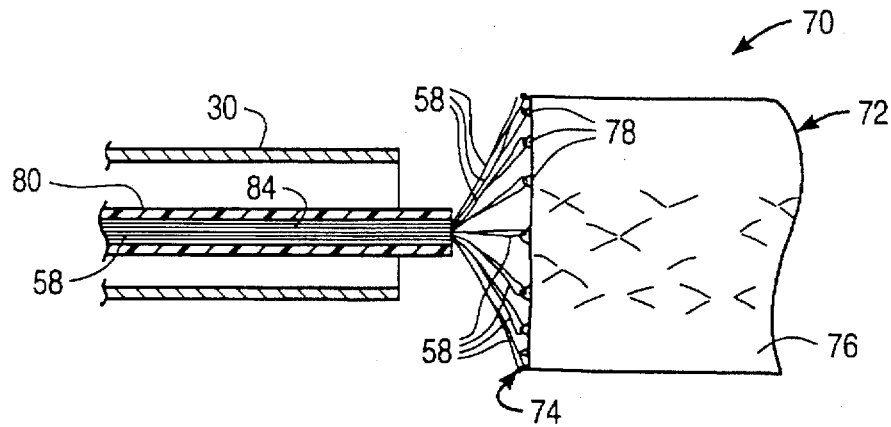
FIGS. 3A–C are cutaway side views of a compression system according to the principles of the present invention.
Figure 3B:
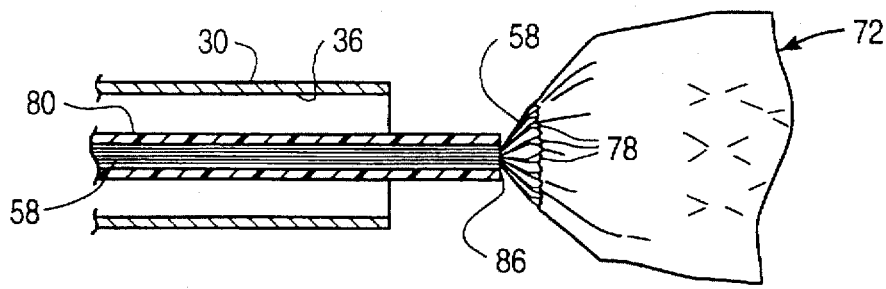

The use of the filament loops and the outer sheath to compress a prosthesis will be described with reference to FIGS. 3A–3C. A simplified prosthesis compression system 70 comprises a tubular body 80 having a distal end 86 and a plurality of filament loops 58 which pass through a portion of a prosthesis. Here, an externally lined prosthesis 72 includes a perforate frame 74 covered by a tubular liner 76. The perforations of frame 74 which allow radial expansion also define proximally oriented apices 78, here shown extending axially beyond the liner. It should be understood that such frame apices may be used even if the liner extends axially beyond the frame. The apices may alternately be defined by separate eyelets at the proximal end of the frame, or the filament loops may instead pass through liner 76 or engage some alternative structure of the prosthesis.

Figure 4:
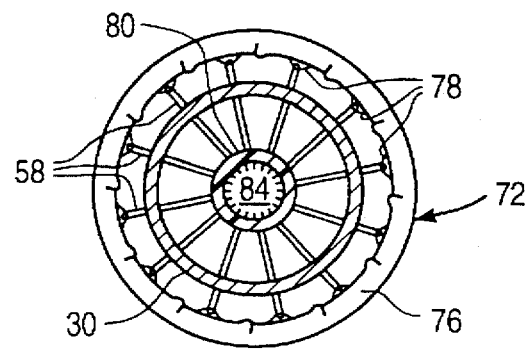
FIG. 4 is a cross-sectional view looking distally toward the prosthesis as the tensioned loops begin to radially compress a proximal end of the prosthesis, according the principles of the present invention.

The ends of filament loops 58 extend into a lumen 84 of tubular body 80, so that tensioning the loops draws the prosthesis radially inward at the apices. Advantageously, the tensioned loops compress the end of the prosthesis directly by application of a roughly radial inward tension force, as is seen most clearly in FIG. 4.

Optionally, the number of loop ends passing through the lumen may be reduced by attaching one end of each loop to the tubular body 80 adjacent its distal end. Alternatively, the loops may be formed from a continuous filament which extends into and out of lumen 84 only a short distance, in which the loops within the lumen are coupled to pull wire, a secondary filament loop, or the like. Generally, however, it is preferable that some end attached to each loop extends proximally through the tubular body to facilitate detaching of the prosthesis, which may conveniently be accomplished by cutting an end of the filament loop and drawing the filaments proximally from the apices 78 and through the lumen. The filaments themselves will typically comprise a high strength flexible yarn or monofilament, preferably comprising polyester, suture, wire, or the like.

Figure 3C:
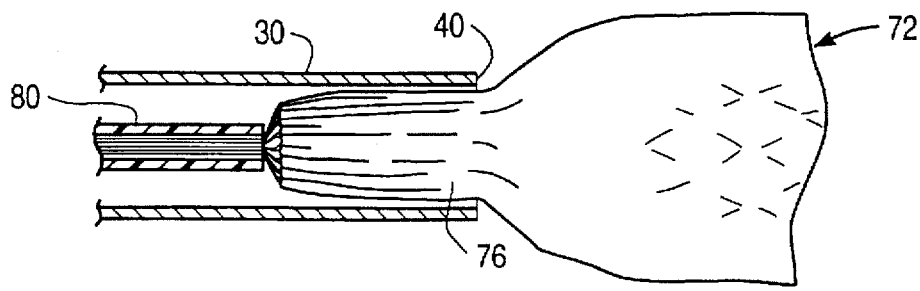

Once the proximal end of the prosthesis has been radially compressed by the filament loops to less than the inner diameter of lumen 34 of sheath 30, the sheath may then be advanced distally (or the prosthesis slid proximally) to compress the remainder of externally lined prosthesis 72, as shown in FIG. 3C. Conveniently, the relative motion between the prosthesis and the sheath may be assisted by maintaining tension in loops 58 to hold the prosthesis, and by moving tubular body 80 relative to sheath 30. Advantageously, the liner is disposed between the frame and the sheath to reduce prosthesis\sheath friction. Nonetheless, substantial friction forces may be produced, particularly at the distal end 40 of sheath 30.

Where the prosthesis is being compressed and loaded into the sheath for later insertion into a body lumen, a fixed radially flared structure adjacent distal end 40 will facilitate smooth compression and avoid damaging the prosthesis as it enters lumen 36. Loading of prostheses which include shape memory alloys can be further facilitated by maintaining the prosthesis at a temperature substantially below the transition temperature to minimize the resilient expansive force of the frame.

Unfortunately, maneuvering a catheter having a large fixed flared structure within a body lumen would be difficult, while substantial reductions in temperature of prostheses which are deployed within a body lumen could harm adjacent tissues. Furthermore, it is often advantageous to support the liner with an external frame, for example, to provide a smooth prosthetic lumen for endovascular applications. Hence, the outer surface of the liner may not be smooth, complicating the recapture of such externally supported prosthesis from a body lumen.

Figure 5A:
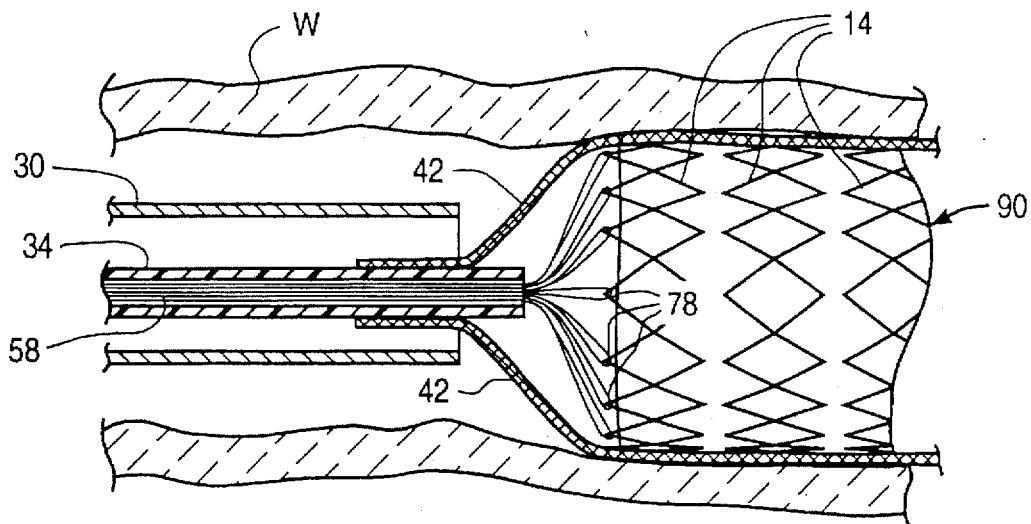
FIGS. 5A–C are cutaway views illustrating the recapture of an expanded prostheses from within a body lumen by tensioning a plurality of filament loops to compress the proximal end of the prosthesis, and by advancing an outer sheath to compress the prosthesis within a plurality of axial runners, according to the principles of the present invention.
Figure 5B:
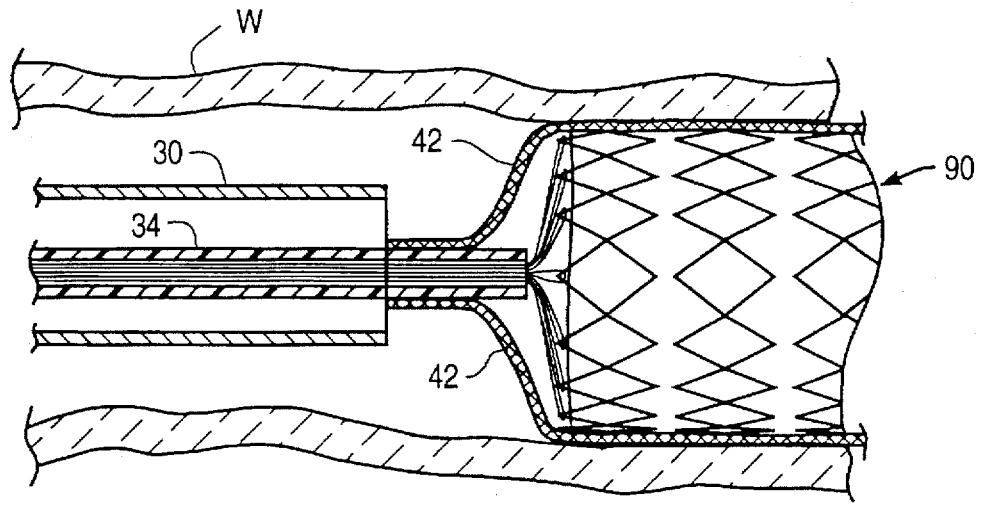
Figure 5C:
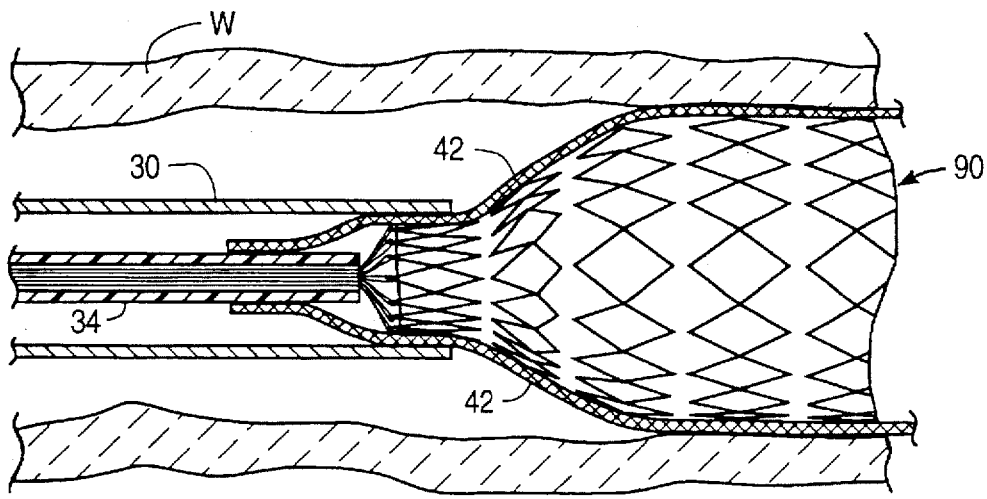

For the above reasons, the runners of the delivery catheter of FIG. 2 are advantageous for recapturing deployed prostheses from within body lumens, particularly externally supported prostheses, as will be understood with reference to FIGS. 5A–C. When an externally supported prosthesis 90 is deployed from sheath 30, the runners flex outward around the expanding prosthesis, remaining between the prosthesis and a body lumen wall W. Ring frames 14 contact the runners and engage wall W in the gaps between the runners. The proximal ring frame 14 defines apices 78, through which loops 58 pass in the initially deployed configuration illustrated in FIG. 5A.

As more fully explained in application Ser. No. 08/475, 200 (Attorney Docket No. 16380-001130), previously incorporated by reference, the runners may then be withdrawn proximally, as the prosthesis will remain anchored to wall W between the runners. As described above, the filament loops 58 may also be cut and removed from the proximal end, allowing the removal of the delivery system.

However, if fluoroscopy (or any other imaging or sensing modality) indicates that the prosthesis is improperly sized or placed, or if it is otherwise desired to recapture the prosthesis before the runners and loops have been withdrawn, loops 58 may be tensioned to radially compress the proximal end of the prosthesis as described above. The extended runners then effectively provide a radially flared structure, facilitating the smooth compression of externally supported prosthesis 90 by sheath 30. Furthermore, the runners are preferably drawn proximally into the sheath together with the prosthesis. The runners distribute the expansive load of the ring frames and slide smoothly within the end of the sheath, substantially decreasing the friction which must be overcome to recompress the prosthesis. Generally, recompression is accomplished by holding the prosthesis and runners in position while the sheath is advanced distally. This helps to avoid damage to wall W caused by movement of the expanded prosthesis or runners.

A wide variety of alternative selectively flareable catheter structures might be used several of which are described in co-pending U.S. patent application Ser. No. 08/290,021 (Attorney Docket No. 16380-001100), the full disclosure of which is also incorporated herein by reference.

As illustrated in FIG. 6, a simple fixed flared structure 100 may be removably disposed at the distal end of the sheath to facilitate loading. Optionally fixed flared structure 100 may be used in combination with axial runners, particularly when loading externally supported stent-grafts into delivery systems prior to deployment. This fixed flared structure is generally removed prior to deployment.

Alternatively, a selectively flarable structure may remain attached to the sheath during deployment. Also shown in FIG. 6 is a the use of the present invention to facilitate loading of removable prosthetic cartridge 102, including a sheath extension 104 (which couples to proximal sheath 106 at sheath coupling 108) and a tubular body extension 110 (which couples to proximal tubular body 112 at body coupling 114). Conveniently, a prosthesis loading system including proximal sheath 106, proximal body 112, and fixed flared structure 100 may be used to load the prosthetic cartridge 102 in the operating room prior to the deployment procedure. This avoids shipping and storing the prosthesis in a compressed configuration, thereby promoting resilient expansion of the prosthesis to its full diameter when it is released. Surprisingly, loading a prosthesis having a shape memory alloy frame at standard operating room temperatures may actually reduce stress and damage to the frame when compared to conventional cold compression. Once the cartridge is loaded, it is detached from the loading system and disposed at the distal end of a delivery catheter having a sheath and tubular body with suitable connectors. Filament loops 58 may be threaded through the tubular body to facilitate cutting and withdrawal of the loops as described above, or some remote disengagement mechanism may alternatively be provided.

Referring finally to FIG. 7, an alternative tubular body 120 includes a lumen 122 extending through a proximal handle 124. Loops 58 pass through the frame of prosthesis 72, each loop having one end identified here as an A end, and another identified as a B end. The A ends are attached to tab 128 of proximal handle 124, while the B ends are attached to tab 126. Conveniently, cutting of the A ends adjacent tab 128 (or alternatively, the B ends adjacent tab 126) allows the tubular body to be withdrawn proximally, the tabs keeping the loop ends clearly organized to prevent inadvertently displacing the prosthesis with an uncut loop.

Although the foregoing invention has been described in some detail by way of illustration and example, for purposes of clarity of understanding, it will be obvious that certain changes and modifications may be practiced within the scope of the appended claims.

What is claimed is:

1. An endoluminal prosthesis system comprising:
   a tubular body having a lumen;
   a radially compressible endoluminal prosthesis having an end with a plurality of engageable structures radially disbursed thereabout;
   a plurality of tensionable flexible filament loops, wherein each loop extends radially from the lumen of the tubular body to engage an engageable structure and returns back toward the tubular body so that tensioning the loops draws the end of the prosthesis radially inward toward the lumen; and
   a sheath which is slidable distally over the prosthesis when the loops are tensioned to compress the prosthesis adjacent the engageable structures.

2. A prosthesis system as claimed in claim 1, wherein each loop engages a single engageable structure.

3. A prosthesis system as claimed in claim 2, wherein the prosthesis comprises a perforate frame supporting a liner, wherein the engageable structures comprise a plurality of N proximally oriented frame apices and adjacent perforations through the frame, and wherein the loops comprise an associated plurality of N loops.

4. A prosthesis system as claimed in claim 1, further comprising a radially flareable structure disposable adjacent to a distal end of the sheath to facilitate smooth compression of the prosthesis when the loops draw the prosthesis proximally into the sheath.

5. A prosthesis system as claimed in claim 4, wherein the flareable structure comprises a plurality of elongate runners which are distally extendable from within the sheath over the end of the prosthesis to slide between the sheath and the prosthesis while the prosthesis is compressed.

6. A prosthesis system as claimed in claim 5, wherein the runners are affixed to the tubular body.

7. A prosthesis system as claimed in claim 5, wherein the prosthesis comprises a frame disposed over a tubular liner.

8. A prosthesis system as claimed in claim 8, further comprising a fixed flared structure disposed at the distal end of the sheath to facilitate compression of the prosthesis prior to deployment.

9. A prosthesis system as claimed in claim 7, further comprising a proximal tubular body and a proximal sheath, wherein the tubular body comprises a tubular body extension having a connector for detachable attachment to the proximal tubular body, and wherein the sheath comprises a sheath extension having a connector for detachable attachment to the proximal sheath, the tubular body extension and sheath extension defining a prosthesis cartridge which is detachable from the fixed flared structure, proximal tubular body, and proximal sheath after the prosthesis is compressed within the sheath extension, and which is coupleable to a delivery catheter for deployment of the prosthesis within a body lumen.

10. An endoluminal prosthesis system as claimed in claim 1, wherein each loop extends proximally through the lumen of the tubular body for tensioning of the loops and compressing the prosthesis from a proximal end of the tubular body.

11. An endoluminal prosthesis system as claimed in claim 10, wherein the prosthesis is detachable from the loops by severing the loops proximally of the tubular body and withdrawing the loops proximally from the prosthesis.

12. An endoluminal prosthesis system comprising:
    a tubular body having a lumen, a proximal end, and a distal end;
    a radially compressible endoluminal prosthesis having a proximal end with a plurality of proximally oriented apices radially disbursed thereabout; and
    a plurality of flexible filament loops, wherein each loop extends radially outward from the distal end of the tubular body, engages an apex of the prosthesis, returns radially inward back to the tubular body, and passes through the lumen to the proximal end of the tubular body; and
    a sheath which is slidably disposable over the tubular body;
    wherein tensioning the loops from the proximal end of the tubular body draws the apices of the prosthesis radially inward to facilitate advancing the sheath distally over the prosthesis so as to radially compress the prosthesis.

13. An endoluminal prosthesis as claimed in claim 12, further comprising a plurality of elongate flexible runners extending distally from the tubular body, wherein the runners are extendable out from the lumen of the sheath and over the prosthesis so as to slide proximally into the sheath over the prosthesis and facilitate compressing the prosthesis.

* * * * *